United States Patent [19]

Shubkin

[11] 4,218,330

[45] Aug. 19, 1980

[54] LUBRICANT

[75] Inventor: Ronald L. Shubkin, West Bloomfield, Mich.

[73] Assignee: Ethyl Corporation, Richmond, Va.

[21] Appl. No.: 919,265

[22] Filed: Jun. 26, 1978

[51] Int. Cl.² .................. C10M 1/48; C10M 1/16
[52] U.S. Cl. .................................. 252/46.6; 252/47; 252/47.5; 585/13; 585/18; 585/255
[58] Field of Search ............... 252/59, 46.6, 47, 47.5; 260/676 R

[56] References Cited

U.S. PATENT DOCUMENTS 3,149,178   9/1964   Hamilton et al. .................. 252/59 X Primary Examiner—Paul F. Shaver
Attorney, Agent, or Firm—Donald L. Johnson; Robert A. Linn; Joseph D. Odenweller

[57] ABSTRACT

Hydrogenated dimers of $C_{12-18}$ alpha olefins (e.g. 1-tetradecene) made using a Friedel-Crafts catalyst (e.g. $BF_3$ promoted with water) have low pour points, low volatility and viscosities which make them suitable as crankcase lubricants for internal combustion engines.

18 Claims, No Drawings

LUBRICANT

BACKGROUND OF THE INVENTION

Oligomerized α-olefins have been known for many years to be effective synthetic lubricating oils. Hamilton, U.S. Pat. No. 3,149,178, describes oligomers of $C_{6-12}$ α-olefins made using a Friedel-Crafts catalyst, a peroxide catalyst or thermal treatment. Hamilton teaches that dimers are unsuitable and it is necessary to remove dimers from the composition in order to avoid having a hydrogenated product with an excessively high pour point. For example, the pour point of an α-decene oligomer containing dimer made using a peroxide catalyst increased from less than $-65°$ C. to $+35°$ C. upon hydrogenation.

Smith et al, U.S. Pat. No. 3,682,823, teach a method of avoiding the above catastrophic increase in pour point without the necessity of removing dimer by using an alkali metal tetrahaloalanate.

Brennan, U.S. Pat. No. 3,742,082, discloses a process for dimerizing $C_{6-10}$ α-olefins using a boron trifluoride catalyst promoted with phosphoric acid or water. The hydrogenated products are useful as fluid lubricants for industrial applications. The reported products have a 210° F. viscosity of 2.01–2.07 cs, making them too fluid for use in engine crankcase lubricating oil. For example, the lowest lubricating oil grade is SAE 5W which has a viscosity at 100° C. of 3.8 cs minimum (SAE handbook).

SUMMARY OF THE INVENTION

It has now been discovered that olefin oligomer suitable for use as crankcase lubricants can be made by dimerizing a $C_{12-18}$ olefin or olefin mixture in which the olefins are predominantly alpha, distilling out monomer and hydrogenating the residual product which is mainly dimers with minor amounts of trimers and higher oligomers.

DESCRIPTION OF THE PREFERRED EMBODIMENT

A preferred embodiment of the invention is a hydrogenated olefin oligomer consisting mainly of dimers of $C_{12-18}$ predominantly alpha olefins having a viscosity above about 3.0 cs at 100° C., a pour point below 0° C. and low volatility suitable for use in crankcase lubricants for internal combustion engines, said oligomer being made by the process comprising contacting a $C_{12-18}$ predominantly alpha olefin or mixture thereof, with the proviso that the average carbon number of said olefin is at least 13, with a Friedel-Crafts catalyst at a temperature of about 20°–200° C. until the reaction mixture excluding monomer is predominantly dimer, distilling to remove monomer and hydrogenating.

The olefins from which the oligomers are made contain from 12 to 18 carbon atoms. Minor amounts outside this range can be tolerated as long as they do not adversely affect the physical properties of the oligomers. Suitable olefins are dodecene, tridecene, tetradecene, pentadecene, hexadecene, heptadecene and octadecene. Pure dodecene is not suitable in making a useful crankcase lubricant according to the present invention. Dodecene leads to products which are too volatile. When dodecene is used it should be in a mixture of olefins containing higher olefins, e.g. tetradecene, hexadecene and the like. The amount of dodecene in the mixtures should not exceed an amount which would give a resulting average carbon number less than 13. "Average carbon number" is the sum of the products obtained by multiplying the mole percent of each olefin by the number of carbon atoms in the olefin. For example, in a mixture of 25 mole percent dodecene-75 percent tetradecene, the average carbon number should be $(0.75 \times C_{14}) + (0.25 \times C_{12}) = 13.5$. This proviso is applicable to all olefin starting materials containing dodecene.

More preferred olefins used as starting materials contain 12–16 carbon atoms and mixtures thereof with the above stated proviso regarding dodecene.

In a highly preferred embodiment the starting olefins contain a major amount, that is, over about 50 mole percent, of tetradecene, the balance being substantially dodecene and/or hexadecene.

The starting olefins are predominantly alpha olefins, that is, linear terminal olefins. By predominantly is meant that they contain over about 50 mole percent, preferably over 75 mole percent of α-olefins. It would be very desirable to use pure α-olefins, but commercially available α-olefins contain minor amounts of internal olefins and vinylidene olefins. It has been found that in making the present dimers fairly large amounts of internal olefins can be tolerated without adversely affecting the physical properties of the oligomer. It would appear that either the α-olefin in the commercial olefins can react with the internal olefins or that the internal olefins are in equilibrium with α-olefins and that as the α-olefins react, more internal olefins are isomerized to α-olefins. It is not necessary to understand the mechanism to successfully use the present invention.

Accordingly, the starting olefins are $C_{12-18}$ predominantly α-olefins with the proviso that the average carbon number is at least 13. More preferably, the starting olefins are $C_{12-16}$, predominantly alpha olefins. In a highly preferred embodiment the starting olefin is predominantly alpha and mainly tetradecene. Still more preferably, the starting olefins are predominantly alpha and consist essentially of at least 50 mole percent tetradecene, the balance being dodecene and/or hexadecene. In a most preferred embodiment, the starting olefins are predominantly alpha and are at least 75 mole percent tetradecene, the balance being dodecene and/or hexadecene.

The oligomers consist mainly of dimers and can be made by contacting the starting olefin with a Friedel-Crafts catalyst. Representative Friedel-Crafts catalysts are $BF_3$, $BCl_3$, $AlCl_3$, $AlBr_3$, $SnCl_4$, $GaCl_3$ and the like.

The preferred Friedel-Crafts catalyst is boron trifluoride. The amount of boron trifluoride should be at least about 0.002 moles per mole of olefin. Preferably, the boron trifluoride is added in an amount which saturates the reaction mixture. A facile method of doing this is to maintain a small boron trifluoride sparge into the liquid phase periodically or during the entire course of the reaction.

To be effective, boron trifluoride is used in combination with a promoter. Many promoters for boron trifluoride are known. They include water, alcohol, ethers, glycols, alkoxy glycols, fatty acids, fatty acid esters, ketones, aldehydes, $H_3PO_4$, HF and the like. The most widely used boron trifluoride promoters are water and alcohol, for example, $C_{1-12}$ alkanols such as methanol, ethanol, isopropanol, hexanol, 2-ethylhexanol and dodecyl alcohol.

Only a minor amount of promoter is needed. A useful range is about 0.002 to 0.040 moles per mole of olefin.

The amount of boron trifluoride is discussed above. As a further consideration, the amount of boron trifluoride depends to some extent on the type and amount of promoter. In general, the boron trifluoride should be in molar excess of the amount of promoter. As stated above, this is most readily accomplished by a slow sparge of BF₃ gas into the liquid phase or by using a closed reactor and a small BF₃ pressure.

The oligomer reaction can be carried out at about 20°–200° C. However, in order to maximize dimer it is preferred that the temperature be at least 50° C. Thus, a preferred temperature range is about 50°–200° C. A more preferred temperature range is about 50°–150° C. Very good results have been obtained at a temperature of about 75°–125° C.

The reaction can be conducted at atmospheric pressure or at elevated pressures up to 1,000 psig. At higher temperatures pressure helps keep the catalyst and promoter in the reaction medium.

The reaction is carried out until the reaction mixture, excluding monomer, is mainly dimer. The period should be long enough such that a substantial amount of dimer has formed, e.g. at least 30 wt %. A useful time range is about one to eight hours. At the more preferred temperature using a BF₃-water catalyst system, excellent results are achieved in about two to four hours.

The oligomer mixture after the reaction contains unreacted monomer, dimer and some higher oligomers (e.g. trimers). The amount of monomer remaining depends to some extent on how long the reaction is conducted. It is preferred to terminate the reaction when about 25–50 wt % of the mixture is still monomer because this minimizes trimer and higher oligomers. This monomer can be readily recycled to the next reaction as part of the olefin charge. The reaction can be terminated by washing to remove catalyst. Good results are achieved using an aqueous ammonia wash.

The light ends consisting almost entirely of monomers are removed from the mixture by distillation. It is not essential to remove all of the monomer, but very little should remain because it can adversely affect the volatility of the final product. Suitable crankcase lubricants must have low volatility or they will evaporate under use conditions resulting in higher oil consumption.

After stripping monomer the reaction mixture is mainly dimers of the starting olefin or olefin mixture. The individual components contain at least about 26 carbon atoms per molecule. In addition to dimer, the reaction mixture contains trimer and higher oligomers, but it is mainly dimer—that is, it is over 50 wt % dimer, more preferably over 60 wt % dimer. Typically, the mixture is about 75 wt % dimer.

The resultant product is next hydrogenated by conventional methods. Supported nickel catalysts are useful. For example, nickel on a kieselguhr support gives good results. The catalyst can be added to the liquid and stirred under hydrogen pressure or the liquid may be trickled through a fixed bed of the supported catalyst under hydrogen pressure. Hydrogen pressure of about 100 to 1,000 psig at 150°–300° C. are useful.

The resultant hydrogenated oligomer is very useful as a crankcase lubricating oil either as the sole lubricant or as a blending agent in mineral and/or synthetic oils (e.g. synthetic ester oils, alkylbenzenes and the like). Such blends permit the base oil to meet the viscosity requirements for SAE 5W or SAE 7.5W without exceeding the oil consumption limits of the ASTM IIId test. For example, when mineral oils are refined to meet an SAE 5W viscosity specification, the oil will almost always fail to qualify in the IIId test due to excessive oil consumption caused by volatility.

The hydrogenated dimer oligomers are especially useful in blends with mineral oil formulated as multigrade oils. These are oils that meet the low temperature (i.e. −18° C.) SAE viscosity specification for 5W, 10W or 20W oils and also meet the high temperature (i.e. 100° C.) viscosity specifications for SAE 20, 30, 40 or 50 grade oil. These SAE specifications are as follows:

| SAE Visc. Grade | Viscosity Range | |
|---|---|---|
| | Centipoise at −18° C. | Centistokes at 100° C. |
| 5W | 1,250 max | 3.8 min | — |
| 10W | 2,500 max | 4.1 min | — |
| 20W | 10,000 max | 5.6 min | — |
| 20 | — | 5.6 min | 9.3 max |
| 30 | — | 9.3 min | 12.5 max |
| 40 | — | 12.5 min | 16.3 max |
| 50 | — | 16.3 min | 21.9 max |

The hydrogenated dimer oligomers are especially useful in mineral oil blends which meet the 5W or 10W SAE viscosity specifications. The hydrogenated dimer makes up about 3–50, preferably 5–40 wt % of the oil excluding other additives. The mineral oil should be of a lubricating viscosity. Useful mineral oils used in the blends have a viscosity range of about 75–500 SUS at 100° F. Straight mineral lubricating oils which meet these viscosity specifications are very often too volatile and will fail the sequence IIId engine test due to excessive oil consumption. The present hydrogenated dimer oligomers have exceptionally low volatility compared to mineral oils and/or other oligomers of the same viscosity.

The structure of the major component of the hydrogenated dimer oil is

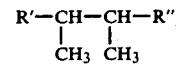

wherein R' and R" are linear alkyl groups containing from 10–16 carbon atoms with the provisio that when R' is a decyl group then R" contain 12–16 carbon atoms. Examples of these components are 11,12-dimethyl tetracosane, 11,12-dimethylhexacosane, 11,12-dimethyl octacosane, 13,14-dimethyl octacosane, 13,14-dimethyl tricontane, 15,16-dimethyl dotriacontane, 17,18-dimethyl tetratriacontane.

The more preferred components are those in which R' is selected from the group consisting of n-decyl, n-dodecyl and n-tetradecyl and R" is selected from the group consisting of n-dodecyl and n-tetradecyl. These are 11,12-dimethyl tetracosane, 11,12-dimethyl hexacosane, 13,14-dimethyl hexacosane, 13,14-dimethyl octacosane, and 15-16-dimethyl triacontane.

Highly preferred components are those in which R' is n-dodecyl and R" is selected from n-dodecyl and n-tetradecyl. These are 13,14-dimethyl hexacosane and 13,14-dimethyl octacosane.

The following examples illustrate the manner of making the present hydrogenated dimer compositions and the physical properties of typical products.

EXAMPLE 1

In a reaction vessel was placed 400 gms of an α-olefin mixture (10.78 wt % $C_{12}$, 88.34 wt % $C_{14}$, and 0.88 wt % $C_{16}$; 80.5% α-olefin, 4.5% internal olefin, and 15.1% vinylidene olefin). This was heated to 85° C. and slow $BF_3$ sparge into the stirred liquid was started. When the liquid was about saturated, 0.25 ml of $BF_3.2$ $H_2O$ complex was added and the stirring continued at 98° C. while slowly injecting $BF_3$ gas into the liquid. At 60 minutes, an additional 0.25 ml $BF_3.2$ $H_2O$ complex was added. At 192 minutes, 0.5 ml $BF_3.2$ $H_2O$ was added. At 240 minutes, $BF_3$ addition was stopped and the reaction quenched with 200 ml water. It was washed with aqueous ammonia and again with water, dried over anhydrous sodium sulfate and filtered. It analyzed by VPC 4.37% $C_{12}$, 41.8% $C_{14}$, 0.17% $C_{16}$, 14.75% $C_{26}$, 32.63% $C_{28}$, and 6.31% higher oligomers. It was distilled to remove light ends (monomer) up to 107.5° C. overhead at 1.9 mm abs. Distillate weighed 124.1 grams, viscosity of residual product was 3.55 cs at 100° C.

The residual product was hydrogenated at 250° C., 500 psig hydrogen using a Ni/kieselguhr catalyst. The hydrogenated oligomer had the following physical properties:

| | |
|---|---|
| Viscosity 100° C. | 3.73 cs |
| Viscosity 40° C. | 15.61 cs |
| Viscosity Index (VI) | 130 |
| Pour Point | −29° C. |

A small weighed sample was placed in an oven at 204° C. for two hours to determine its percent weight loss due to volatility. A weight loss of 25% or less in this test indicates that the oligomer would pass the sequence IIId test. This oligomer gave a 17.6% weight loss.

EXAMPLE 2

In a reaction vessel was placed 115.7 grams of recycle distillate from Example 1 and 284.2 grams of α-tetradecene mixture used in Example 1. Heat and stirring were applied and $BF_3$ sparge was started at 91° C. At 97° C. 0.6 ml $BF_3.2$ $H_2O$ was added to start the reaction. After 215 minutes stirring at 97°–99° C. $BF_3$ sparge was stopped and the reaction quenched with water, washed with aqueous ammonia and again with water, dried and filtered. The mixture analyzed 3.02% $C_{12}$, 41.3% $C_{14}$, 0.3% $C_{16}$, 51.8% $C_{26}+C_{28}$, and 3.3 wt % higher oligomers. This mixture was topped to 133° C. at 1.5 mm abs to remove monomers. Distillate was 111.7 grams, 35.4% of distillation charge. The residual mixture analyzed 34.7% $C_{26}$, 52.36% $C_{28}$ and 12.75% higher oligomers (viscosity 3.65 cs at 100° C.).

The residual dimer mixture was hydrogenated as in Example 1 giving a saturate product having the following physical properties:

| | |
|---|---|
| Viscosity 100° C. | 3.8 cs |
| Viscosity 40° C. | 16.68 cs |
| VI | 119 |
| Pour point | −34° C. |
| Volatility | 20.7% |

EXAMPLE 3

In a reaction vessel was placed 400 grams of a tetradecene/hexadecene α-olefin mixture (68 wt % $C_{14}$, 32 wt % $C_{16}$; 75.5% α-olefin, 5.9% internal olefin, 18.6% vinylidene olefin). While stirring and heating, $BF_3$ injection was started at 79° C. At 95° C., 0.5 ml $BF_3.2$ $H_2O$ was added. The reaction continued with slow $BF_3$ sparge for 275 minutes at 98° C. It was then quenched with water, washed with aqueous ammonia, washed again with water, dried and filtered. It analyzed 0.53% $C_{12}$, 30.84% $C_{14}$, 15.44% $C_{16}$, 22.78% $C_{28}$, 23.5% $C_{30}$ and 6.92% higher oligomer. The mixture was topped in a distillation column to 118° C. overhead at 2.1 mm abs. Viscosity of the residual oligomer was 3.95 cs at 110° C.

The product was hydrogenated as in Example 1, giving a saturated mainly dimer oligomer having the following physical properties:

| | |
|---|---|
| Viscosity 100° C. | 4.15 cs |
| Viscosity 40° C. | 17.9 cs |
| VI | 137 |
| Pour point | −26° C. |
| Volatility | 11.5% |

EXAMPLE 4

In a reaction vessel was placed 400 grams of the dodecene-tetradecene mixture used in Example 1. Heat was applied and at 58° C. $BF_3$ sparge was started. At 74° C. 0.6 ml $BF_3.2$ $H_2O$ was added and the reaction continued at 74°–75° C. for 125 minutes. It was then quenched, washed, dried and filtered as before. It analyzed 5.73% $C_{12}$, 4.38% $C_{14}$, 0.44% $C_{16}$, 8.93% $C_{26}$, 31.44% $C_{28}$ and 9.3% higher oligomers. This mixture was topped to 110° C. at 2 mm abs giving 149.2 gms distillate and 214.9 gms residual product, analyzing 18.65% $C_{26}$, 61.88% $C_{28}$ and 18.46% higher oligomers. Its viscosity was 3.64 cs at 100° C.

The residual product was hydrogenated as before giving a saturated, mainly dimer, oligomer having the following physical properties:

| | |
|---|---|
| Viscosity 100° C. | 3.85 cs |
| Viscosity 40° C. | 15.8 cs |
| VI | 141 |
| Volatility | 16.2% |

EXAMPLE 5

In a reaction vessel was placed 400 grams of the tetradecene-hexadecene α-olefin from Example 3. It was stirred and heated and $BF_3$ sparge started at 73° C. At 85° C. 0.6 ml $BF_3.2$ $H_2O$ complex was added and the reaction continued for 145 minutes at 85° C. The mixture was quenched, washed with aqueous ammonia and water and dried and filtered as before. It analyzed 0.38% $C_{12}$, 33.9% $C_{14}$, 17.03% $C_{16}$, 0.13% $C_{18}$, 19.63% $C_{28}$, 23.4% $C_{30}$ and 5.04% higher oligomers. This was topped to 125° C. at 1.8 mm abs giving a residual dimer analyzing 43.19% $C_{28}$, 49.14% $C_{30}$ and 6.83% higher oligomers. Its viscosity was 3.96 cs at 100° C. It was hydrogenated as before giving a saturated dimer oligomer analyzing:

| | |
|---|---|
| Viscosity 100° C. | 4.17 cs |
| Viscosity 40° C. | 17.65 cs |
| VI | 145 |
| Volatility | 9.9% |

EXAMPLE 6

In a reaction vessel was placed 6 Kg of the tetradecene mixture of Example 1. This was stirred and heated and BF$_3$ sparge started at 75° C. At 78° C. 15 gms BF$_3$.2 H$_2$O complex was added to start the reaction. It was stirred for three hours at 80°–83° C. with BF$_3$ sparge. It was quenched with water, washed with aqueous ammonia, washed with water, dried and filtered. The mixture analyzed 4.34% C$_{12}$, 35.04% C$_{14}$, 15.21% C$_{26}$, 38.16% C$_{28}$ and 7.25% higher oligomers. This was topped to 198° C. at 0.35 mm abs. Its viscosity was 3.68 cs at 100° C. It was hydrogenated as before giving a dimer product having the following physical properties:

| | |
|---|---|
| Viscosity 100° C. | 3.85 cs |
| Viscosity 40° C. | 16.01 cs |
| Viscosity −18° C. | 298.4 cs |
| VI | 137 |
| Pour point | −29° C. |
| Volatility | 16.6% |

EXAMPLE 7

In a reaction vessel was placed 400 ml of the tetradecene-hexadecene mixture used in Example 3. It was oligomerized in the manner of the previous examples using 0.6 ml BF$_3$.2 H$_2$O, continuous BF$_3$ sparge at 84.5°–85° C. for 270 minutes. It analyzed 14.95% monomer, 36% C$_{28}$, 20.6% C$_{30}$, 6.18% C$_{32}$ and 18.8% higher oligomer. It was quenched, washed, dried and filtered as before. It was then topped to 132.5° C. at 1.85 mm abs to remove monomer. Its viscosity was 4.48 cs at 100° C.

This shows that longer reaction periods decrease the amount of unreacted monomer but increase the amount of trimer and higher oligomers resulting in a higher viscosity product. Such products are useful in many applications, for example, as transformer oils or in formulating gear lubricants. The product was not hydrogenated.

EXAMPLE 8

In this example, a mixture of 200 ml of the dodecene-tetradecene of Example 1 and 200 ml of the tetradecene-hexadecene of Example 3 were oligomerized at 85° C. using 0.6 ml BF$_3$.2 H$_2$O and BF$_3$ sparge for 120 minutes. The product analyzed 2.73% C$_{12}$, 38.9% C$_{14}$, 7.8% C$_{16}$, 6.16% C$_{26}$, 24.9% C$_{28}$, 12.79% C$_{30}$ and 6.66% higher oligomers. After washing and drying this mixture was topped to 131.5° C. at 1.9 mm abs to remove monomers. Its viscosity at 100° C. was 3.79 cs. The product was then hydrogenated to give a saturated, mainly dimer, oligomer having the following physical properties:

| | |
|---|---|
| Viscosity 100° C. | 4.0 cs |
| Viscosity 40° C. | 16.79 cs |
| VI | 140 |
| Volatility | 13.5% |

Not all α-olefin dimers have the structure required to give the very desirable physical properties of the present oligomers. For example, similar dimers made using an aluminum alkyl catalyst result in a dimer composition which has an unacceptable pour point. The following table compares the physical properties of two different α-tetradecene dimers, each made using a different catalyst.

| | Unsaturated | | | Hydrogenated | | |
|---|---|---|---|---|---|---|
| | Visc (cs) | | Pour | Visc (cs) | | Pour |
| | 40° | 100° | Pt °C. | 40° | 100° | Pt °C. |
| tri-n-butyl aluminum | 11.80 | 3.45 | +13 | 13.09 | 3.63 | +30 |
| boron trifluoride | 11.44 | 3.06 | −43 | 12.25 | 3.19 | −36 |

As the results show the dimer made using the alkyl aluminum catalyst has a higher viscosity compared to the dimer made using a Friedel-Crafts catalyst. In addition, the dimer made using boron trifluoride (promoted with water) has a pour point that is about 60° C. lower than that of the dimer made using an alkyl aluminum catalyst. These differences prevail whether the dimer is unsaturated or hydrogenated. The sharply lower pour point of the present hydrogenated dimer is believed to be due to the presence of two pendent methyl groups on adjacent carbon atoms as shown in the previous structural formula. Nuclear magnetic resonance (NMR) data is consistent with this structure. The alkyl aluminum catalyzed dimer has a different structure with only a single pendent methyl group.

The hydrogenated dimer oligomers of this invention are ideally suited for use in lubricating oil used in the crankcase of internal combustion engines, both diesel and spark ignited. The viscosity of the present oligomers at 100° C. is 3.0 cs or higher. More preferably, their viscosity is at least 3.3 cs, and most preferably 3.5 cs or higher. The upper viscosity limit depends upon the α-olefin used and the amount of higher oligomers in the product. The more viscous oligomers find use in formulating gear lubricants and in making grease.

The oligomer may be the sole lubricant or may be used in blends with other lubricating oils such as mineral oil, diester synthetic oils, complex ester oils, hindered ester oils and the like.

When used in blends the synthetic dimer oligomer preferably forms about 3–50 wt %, more preferably 5–40 wt %, of the total oil excluding additives. When used in such blends the synthetic dimer oligomer permits a reduction in viscosity without increased volatility. Such blends make it possible to formulate a SAE 5W lubricating oil from the available mineral oil stocks without exceeding the volatility limits of the sequence IIId test. In making such blends the hydrogenated dimer oligomer should have a low viscosity of about 3.0–4.5 cs, more preferably about 3.3–4.3 cs, at 100° C. Usually such blends contain about 10–30 wt % of the present hydrogenated dimer oligomers.

The lubricating oils of this invention are blended to contain various additives which impart beneficial properties to crankcase lubricants. These are conventional lubricating oil additives such as zinc dialkyldithiophosphate (described in U.S. Pat. Nos. 2,680,123; 2,689,220; 2,838,555; and 3,293,181), alkaline earth metal salts of petroleum sulfonic acids, or alkylbenzene sulfonic acid (e.g. Ca, Ba or Mg sulfonates) or overbased alkaline earth metal sulfonates (described in U.S. Pat. Nos. 2,361,476; 2,501,731; 2,807,590; 2,815,370; 2,865,956; 2,895,913; 2,909,563; 2,924,617; 2,956,018; 3,027,325; 3,057,896; 3,105,049; 3,256,186; 3,312,618; and 3,367,865), alkaline earth alkylphenates and sulfurized phenates, ashless dispersants such as the commercial alkenyl-succinamides and imides of ethylene polyamines (described in U.S. Pat. Nos. 3,087,936; 3,154,560; 3,172,892; 3,202,678; 3,216,936; 3,219,666; 3,272,743; 3,272,746; and 3,361,673), alkenylsuccinic acid esters of alkane polyols such as pentaerythritol (described in U.S. Pat. Nos. 3,371,776; 3,381,022; and 3,522,179), Mannich condensation products formed from alkylphenol, formaldehyde, and reactive amines such as tetraethylenepentamine and related Mannich products modified by boronation (described in U.S. Pat. Nos. 3,368,972; 3,413,347; 3,442,808; 3,448,047; 3,539,633; 3,591,598; 3,600,372; 3,634;515; 3,697,574; 3,703,536; 3,704,308; 3,725,480; 3,726,882; 3,736,357; 3,751,365; 3,756,953; 3,793,202; 3,798,165; 3,798,247; and 3,803,039), phosphosulfurized polyolefins such as the reaction product of $P_2S_5$ with polybutenes, alkaline metal salts of phosphosulfurized polyolefins, antioxidants such as 4,4'-methylenebis(2,6-di-tert-butylphenol), 2,6-di-tert-butyl-$\alpha$-dimethylamino-p-cresol, VI improvers such as ethylene-propylene copolymers and polyalkyl methacrylates and the like. All the cited patents are incorporated herein by reference.

EXAMPLE 9

In a blending vessel place 10,000 parts of the hydrogenated dimer mixture from Example 1. To this add sufficient zinc isobutyl amyl dithiophosphate to provide 0.07 wt % Zn, overbased calcium alkylbenzene sulfonate (300 base number) in an amount to provide 1.5 wt % Ca, 500 parts of a commercial polyalkyl methacrylate VI improver, 500 parts of di(2-ethylhexyl)adipate to improve seal swell and 20 parts of 4,4'-methylenebis(2,6-di-tert-butylphenol). Blend the mixture hot and filter to remove solids resulting in a synthetic lubricating oil suitable for use in an engine crankcase.

EXAMPLE 10

In a blending vessel place 2,000 parts of the hydrogenated dimer of Example 6 and 8,000 parts of a 150 SUS neutral mineral oil. To this add zinc isobutyl 2-ethylhexyl dithiophosphate to provide 0.1 wt % Zn, overbased calcium petroleum sulfonate (250 base number) in an amount to provide 0.75 wt % Ca, overbased magnesium alkylbenzene sulfonate (400 base number) in an amount to provide 0.75 wt % Mg and 500 parts of a commercial polyalkyl methacrylate VI improver. Blend the mixture hot and filter to remove solids giving a partial synthetic lubricating oil blend suitable for use in an engine crankcase.

I claim:

1. A hydrogenated olefin oligomer consisting mainly of dimers of $C_{12-18}$ predominantly alpha olefins having a viscosity above about 3.0 cs at 100° C., a pour point below 0° C. and low volatility such that less than 25 weight percent evaporates after two hours at 204° C., said oligomer being suitable for use in crankcase lubricants for internal combustion engines, said oligomer being made by the process comprising contacting a $C_{12-18}$ predominantly alpha olefin or mixture thereof, with the proviso that the average carbon number of said olefin or mixture thereof is at least 13, with a Friedel-Crafts catalyst at a temperature of about 20°–200° C. until the reaction mixture excluding monomer is predominantly dimer, distilling to remove monomer and hydrogenating.

2. An oligomer of claim 1 wherein said predominantly alpha olefins contain 12–16 carbon atoms with the proviso that the average carbon number of said olefins is at least 13.

3. An oligomer of claim 2 wherein said predominantly alpha olefins are mainly tetradecene.

4. An oligomer of claim 3 wherein said predominantly alpha olefins are a mixture consisting essentially of at least 50 mole percent tetradecene and the remainder being dodecene, hexadecene, or mixtures thereof.

5. An oligomer of claim 1 wherein said Friedel-Crafts catalyst is boron trifluoride in combination with a promoter and said temperature is 50°–150° C.

6. An oligomer of claim 5 wherein said promoter is water.

7. An oligomer of claim 6 wherein said predominantly alpha olefins contain 12–16 carbon atoms with the proviso that the average carbon number is at least 13.

8. An oligomer of claim 7 wherein said predominantly alpha olefins are mainly tetradecene.

9. An oligomer of claim 8 wherein said predominantly alpha olefins are a mixture consisting essentially of at least 50 mole percent tetradecene, the balance being dodecene, hexadecene or mixtures thereof.

10. An oligomer of claim 9 wherein said predominantly alpha olefins are a mixture consisting essentially of at least 75 mole percent tetradecene, the balance being dodecene, hexadecene or mixtures thereof.

11. A lubricating oil blend comprising a major amount of mineral oil of lubricating viscosity and a minor amount of about 5–40 weight percent of an oligomer of claim 1.

12. A lubricating oil blend of claim 11 wherein said oligomer is made by the process comprising contacting predominantly alpha olefins containing 12–16 carbon atoms with the proviso that the average carbon number of said olefins are at least 13, with a boron trifluoride catalyst in combination with a promoter at about 50°–150° C. until the reaction mixture excluding monomer is predominantly dimer, distilling to remove monomer and hydrogenating to form a hydrogen saturated oligomer.

13. A lubricating oil blend of claim 12 wherein said predominantly alpha olefins consist essentially of at least 50 mole percent tetradecene, the balance being dodecene, hexadecene or mixtures thereof.

14. A lubricating oil blend of claim 13 wherein said predominantly alpha olefins consist essentially of at least 75 mole percent tetradecene, the balance being dodecene, hexadecene or mixtures thereof.

15. A formulated crankcase lubricating oil composition comprising a hydrogenated dimer oligomer of claim 1, an alkaline earth metal sulfonate and an ashless dispersant selected from the group consisting of alkenylsuccinimides of polyalkylene polyamines, Mannich condensation products or alkylphenols, aldehydes and reactive amines and alkaline succinic acid esters of alkanepolyols.

16. A formulated crankcase oil of claim 15 wherein said hydrogenated dimer oligomer is an oligomer of claim 5.

17. A formulated engine crankcase oil of claim 16 containing a major amount of mineral oil of lubricating viscosity and a minor amount between about 5 and 50 wt % of said hydrogenated dimer oligomer.

18. A formulated engine crankcase oil of claim 17 containing 0.01–0.5 wt % zinc in the form of a zinc dialkyldithiophosphate.

* * * * *